United States Patent [19]

Mitchell et al.

[11] 4,053,534

[45] Oct. 11, 1977

[54] ORGANIC COMPOUND CONVERSION

[75] Inventors: Thomas Owen Mitchell, Trenton; Darrell Duayne Whitehurst, Titusville, both of N.J.

[73] Assignee: Mobil Oil Corporation, New York, N.Y.

[21] Appl. No.: 754,209

[22] Filed: Dec. 27, 1976

Related U.S. Application Data

[60] Division of Ser. No. 681,883, April 30, 1976, which is a continuation-in-part of Ser. No. 443,557, Feb. 19, 1974, Pat. No. 3,980,583.

[51] Int. Cl.$^2$ .................................................. C07C 3/14
[52] U.S. Cl. ............................................. 260/683.15 R
[58] Field of Search ................................ 260/683.15 R

[56] References Cited

U.S. PATENT DOCUMENTS

| | | | |
|---|---|---|---|
| 3,221,002 | 11/1965 | Orzechowski et al. | 252/430 |
| 3,464,929 | 9/1969 | Mitsche | 260/683.15 R |
| 3,804,917 | 4/1974 | Shepard et al. | 260/683.15 R |
| 3,959,400 | 5/1976 | Lucki | 260/683.15 R |

*Primary Examiner*—C. Davis
*Attorney, Agent, or Firm*—Charles A. Huggett; Raymond W. Barclay; Dennis P. Santini

[57] ABSTRACT

Organic compound conversion in the presence of a new class of heterogeneous catalyst is provided. Said new class of heterogeneous catalyst comprises a substrate having a minimum surface area of about 10 m$^2$/g and having pores with a minimum pore diameter of about 5 Angstrom Units, said substrate being modified by at least one amine functional member coordinated to a metal function, said amine functional member acting as a bridging member between said substrate and said metal function.

29 Claims, No Drawings

ORGANIC COMPOUND CONVERSION

CROSS-REFERENCE TO RELATED APPLICATION

This is a division of application Ser. No. 681,883, filed Apr. 30, 1976, which is a continuation-in-part of application Ser. No. 443,557, filed Feb. 19, 1974, now U.S. Pat. No. 3,980,583.

BACKGROUND OF THE INVENTION

1. Field of the Invention

This invention relates to organic compound conversion with a new class of heterogeneous catalyst having exceptional chemical and thermal stability, high upper reaction temperature limits and good catalytic activity for conversion of organic compounds, said catalyst comprising a substrate which is modified by at least one amine functional member coordinated to a metal function, said amine functional member acting as a bridging member between said substrate and said metal function.

2. Description of Prior Art

There has long been a need for effective, commercially practicable transition metal catalysts for such reactions as hydrogenation, hydroformylation, carbonylation, dimerization and others. Early catalysts developed for such purposes were homogeneous catalysts which suffered from, among other things, the expense of recovering, repurifying and recycling said catalysts. Changes in selectivity and reactivity were often brought about by varying ligands and by changes in operating conditions, such as, for example, temperature, pressure, reactant ratios, reaction rates and others. Catalyst losses were often so high that relatively inexpensive metals such as cobalt were used, even though such catalysts required severe operating conditions. Catalysts which were effective under somewhat milder conditions, such as rhodium complexes, were much more expensive (of the order of $10^3$ times as expensive), and, therefore, to insure low catalyst loss, created the requirement of costly recovery systems.

More recently, a number of heterogeneous catalysts have been developed (Belgium Pat. No. 721,686) which demonstrate activities and selectivites for certain reactions, such as, for example, hydroformylation. Those heterogeneous catalysts are comprised of transition metal complexes on ligands bonded to macroporous resins and show superior catalytic results in certain reactions, such as hydroformylation, when compared to their homogeneous analogues. However, the utility of said heterogeneous catalysts is limited by the relatively low chemical and thermal stability of the resin supports therein.

Another class of heterogeneous catalyst has been developed comprising complexed transition metals on phosphine ligands bonded to inorganic oxide surfaces (Dutch Pat. No. 7,018,453 and British patent specification No. 1,275,733). This class of catalysts has been shown to be useful in the hydroformylation reaction (Dutch Pat. No. 7,018,322).

The instant invention of organic compound conversion with a new class of heterogeneous catalyst, which catalyst comprises a substrate having a minimum surface area of about 10 m$^2$/g and having pores with a minimum pore diameter of about 5 Angstrom Units, said substrate being modified by at least one amine functional member coordinated to a metal function, said amine functional member acting as a bridging member between said substrate and said metal function, is demonstrated to provide benefits unmatched by use of prior resin-bound heterogeneous catalysts or oxide-bound phosphine functionalized heterogeneous catalysts. The catalyst for use in this invention has enhanced organic compound conversion activity, e.g. olefin isomerization activity, relative to other oxide-bound or resin-bound complexes. With respect to catalytic activity, the catalyst for use herein shows dual-functional catalytic activity, e.g in which an olefin is hydroformylated to an aldehyde which is then converted by an acid functionality of the catalyst to an acetal in the presence of an alcohol.

SUMMARY OF THE INVENTION

In accordance with the present invention there is provided novel method of organic compound conversion which comprises contacting said organic compound under organic compound conversion conditions with a catalytically effective amount of a catalyst comprising a substrate consisting of a porous solid refractory inorganic oxide, e.g. zeolite, having a minimum surface area of about 10 m$^2$/g, preferably a minimum of about 200 m$^2$/g, and having pores with a minimum pore diameter of about 5 Angstrom Units, preferably a minimum of about 100 Angstrom Units, said substrate being modified by at least one amine functional member coordinated to a metal function, said amine functional member acting as a bridging member between said substrate and said metal function.

DESCRIPTION OF PREFERRED EMBODIMENTS

The catalyst for use in the instant invention is a new class of heterogeneous catalyst displaying exceptionally valuable properties in organic compound conversion processes. The catalyst comprises a substrate having certain specific and essential modifications. The substrate may be one of a number of solid porous inorganic oxides, e.g. zeolites, having surface hydroxyl groups, provided that said inorganic oxide has a minimum surface area of about 10 m$^2$/g and pores with a minimum pore diameter of about 5 Angstrom Units. Non-limiting examples of said substrate include those having a major component of silica or alumina or both, such as, for example, alumina, siliceous materials, open lattice clays and crystalline aluminosilicates.

Non-limiting examples of siliceous materials useful as said substrate include silica and combinations thereof with oxides of metals of Groups II-A, III-A, III-B, IV-A, IV-B and V-B of the Periodic Table of Elements, such as, for example, silica-alumina, silica-magnesia, silica-zirconia, silica-thoria, silica-berylia, silica-titania, as well as ternary compositions of silica, such as, for example, silica-alumina thoria and silica-alumina-zirconia.

Non-limiting examples of crystalline aluminosilicate materials useful as the substrate of the catalyst include the synthetic zeolites, X, Y, ZSM-4, ZSM-5, ZSM-11, ZSM-35, ZSM-38 and others, and naturally occurring zeolites, such as erionite, faujasite, mordenite and others.

Non-limiting examples of open lattice clays useful as the substrate of the catalyst include bentonite and montmorillonite and others.

The solid porous refractory oxide for use herein as said substrate may have deposited or exchanged thereon one or more of various metal components in keeping with the spirit and scope of the invention. For example, alumina and a siliceous material as above defined may have deposited thereon a metal of Groups VI-B or VIII of the Periodic Table of the Elements, e.g. Co and Mo, or an oxide of such a metal, e.g. $MoO_3$ and $CrO_3$. Also, for example, a crystalline alumino-silicate for use herein may have exchanged thereon hydrogen or metal cations of Groups IA-VIII of the Periodic Table, especially metals of Groups II and III, including the rare earth metals, tin, lead, metals of the actinide series, antimony, bismuth and chromium or combinations thereof. Further, a crystalline aluminosilicate for use herein may be incorporated into a naturally-occurring inorganic material, such as, for example clay and metal oxides.

Specific modifications to the substrate chosen for the catalyst include at least one amine functional member, containing the element silicon, coordinated to a metal function, said amine functional member acting as a bridging member between said substrate and said metal function. Said amine function exists, when in a bridging position between said substrate and said metal function, as a ligand covalently bonded to said substrate. The functionalization, i.e. covalently bonding said amine ligand to said substrate, of said substrate can be either exterior or interior of said substrate.

The metal function complexed to said amine ligand bridging member may be any one or more of a series of metals recognized in the art as transition metals selected from the group consisting of Group VIII metals of the Periodic Table of Elements. Non-limiting examples of such metals include iron, cobalt, nickel, ruthenium, rhodium, palladium, iridum, platinum and osmium.

Said metal functions for complexing to said amine ligand functions may be in the form of, by way of non-limiting examples, halides, e.g. fluorides, chlorides and iodides; oxides; sulfides; sulfates, carbonates, carboxylates and nitrates.

Non-limiting examples of said catalyst, therefore, include the following, wherein X is said complexed metal function:

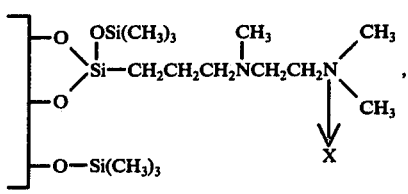

(1)

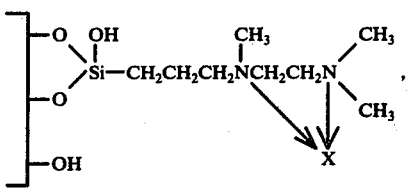

(2)

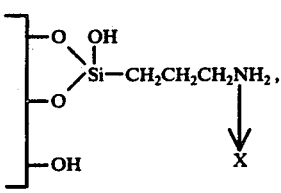

(3)

(4)

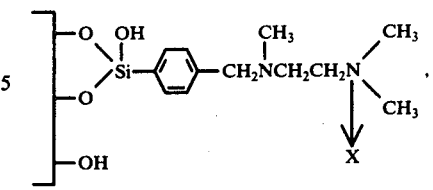

(5)

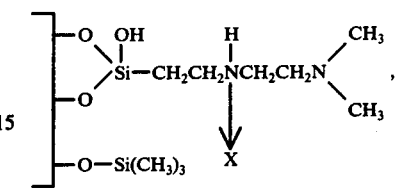

(6)

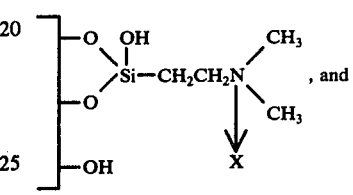

(7)

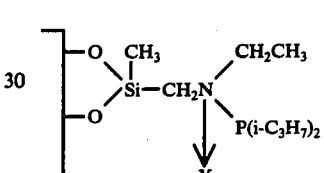

In synthesis of the catalyst for use in the present invention the general method may be employed in which a suitable substrate, i.e. a porous solid inorganic refractory oxide, having surface hydroxyl groups, e.g., silica, silica-alumina, alumina, a natural zeolite such as, for example, erionite, and a synthetic zeolite such as, for example, ZSM-5, is allowed to react with a suitable alkyl substituted compound of silicon, in acid or base catalysis, if desired. The above alkyl compounds must contain a functional group on the silicon atom, as for example, hydro, amino, amido, carboxy, alkoxy or halogen which will condense with hydroxyl groups to give a covalent bond. Said alkyl compound must also have on the alkyl moiety one or more ligands (or groups which may be converted to ligands via conventional organic chemistry) suitable for bonding transition metal complexes which have desirable catalytic properties, i.e. metals from Group VIII.

More specifically, the method of preparing a catalyst for use herein may include suspending said porous solid inorganic oxide substrate in a solution of an appropriate amino alkyl substituted compound of silicon, for example a silane, in xylene or another suitable solvent, refluxing the resulting mixture for a suitable time, such as, for example, 2-6 hours, cooling the mixture and washing it with a suitable solvent, such as, for example, hexane, in which said silane is soluble, and then drying the resultant product in a vacuum, such as, for example, in a vacuum oven, at an elevated temperature of, for example, 100° C to about 150° C. The individual steps of this method may be separated by long periods of time without detrimental results.

For preparation of the insoluble oxide-bound metal compound complex, a solution of soluble coordination compound having at least two ligands connected to at least one central metal atom is mixed with the insoluble functionalized oxide. Upon mixing of the coordination compound with the functionalized oxide, the two react with the functional group of the oxide replacing one or more of the ligands of the coordination compound, thereby chemically bonding the coordination compound to the oxide through at least one bond which joins the central metal atom to a functional group.

The ligands of the soluble coordination compound may be ionic, neutral or mixed ligands. Anionic ligands include chloride, bromide, iodide, cyanide, nitrate, sulfate, acetate, sulfide, and trichlorostannite ligands. Neutral ligands include water, ammonia, phosphine, carbon monoxide, olefin, and diolefin ligands.

The central metal atom of the soluble coordination compound may be any Group VIII metal. Preferably, the central metal atom is selected from the group consisting of platinum, palladium, rhodium, ruthenium, osmium and iridium. Usually, the soluble coordination compound will have one central metal atom. However, it may have two central metal atoms, either the same or different.

Examples of suitable coordination compounds are potassium tetrachloropalladite, chloroplatinic acid, rhodium trichloride trihydrate, dichlorobis (triphenylphosphine) palladium (II), dichlorotetrakis-(triphenylphosphine) ruthenium (II), chlorobis(triphenylphosphine) rhodium (I), tricarbonylbis (triphenylphosphine) ruthenium (O), iodocarbonylbis (triphenylphosphine) iridium (I), potassium tetranitroplatinate (II), tetra (pyridine) platinum (II) tetrabromoplatinate, tetraaminepalladium (II) chloride, di-mu-chlorodichlorobis (triethylarsine) diplatinum (II), di-mu-thiocyanatodithiocyanatobis(tripropylphosphine) diplatinum (II) and potassium trichloro (trichlorostannato) platinite (II).

Solvents for the soluble coordination compounds include water, methanol, ethanol, butanol, acetic acid, chlorinated hydrocarbons such as chloroform, various ethers such as diethyl ether, acetone, and dimethyl sulfoxide.

The solution of the soluble coordination compound and the functionalized oxide, upon mixing, is subjected to agitation at a temperature and for a time to effect bonding of a desired amount of the coordination compound to the functionalized oxide. Agitation may be effected simply by stirring. However, other conventional means of agitation may be employed. The temperature may range from between room temperature to just below the decomposition temperature of either the coordination compound or the amine functional bridging member. Preferably, temperatures between room temperature and the boiling point of the solvent for the coordination compound are employed. The rate at which the coordination compound reacts with the functionalized oxide depends, of course, on the temperature, the rate increasing with temperature. The time of agitation may range from a fraction of an hour, say one-quarter of an hour, to several hours, say 12 hours, or even one or more days, say 3 days.

Following reaction of the coordination compound and the functionalized oxide, the resulting insoluble oxide-bound metal compound complex is separated from the product mixture. Separation may be by any conventional means. Thus separation may be by settling of the complex and decantation of the liquid portion of the product mixture. Separation may also be made by filtration or centrifugation. The complex then may be washed to remove adhering and absorbed solvent and any unreacted dissolved coordination compound. Washing, for example, may be with water, followed by ethanol, and then with ether. Thereafter, the complex may be dried.

The insoluble oxide-bound metal compound complex will be insoluble in the materials, heretofore mentioned, in which the original oxide portion of the complex is insoluble. Thus, the complex will be insoluble in water, hydrocarbons such as benzene, alcohols, aldehydes, ethers, ketones, organic acids, carbon disulfide, thiols, amines, and others. Further, the metal of the coordination compound being bonded chemically to the functionalized oxide will also be insoluble in these same materials.

The final catalyst for use herein may comprise 0.01 to 30 percent, preferably 0.1 to 10 percent, by weight of metal; 0.1 to 25 percent, and preferably 2 to 10 percent, by weight of amine-functional ligand; and about 60 to 99.9 percent by weight of oxide. The sum of the amount of the ligand and metal preferably should not exceed 25 percent.

The production of an insoluble oxide-bound metal compound complex may be illustrated employing, as a soluble coordination compound having anionic ligands, potassium tetrachloropalladite, $K_2PdCl_4$, and an insoluble functionalized silica. The coordination compound is dissolved in water and then mixed with the functionalized oxide. The coordination compound reacts with the functionalized oxide according to the following equation:

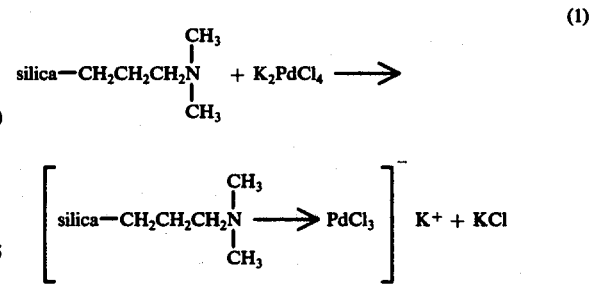

The $K^+$ is not chemically bonded to the Pd. The complex of equation (1) may then react as follows:

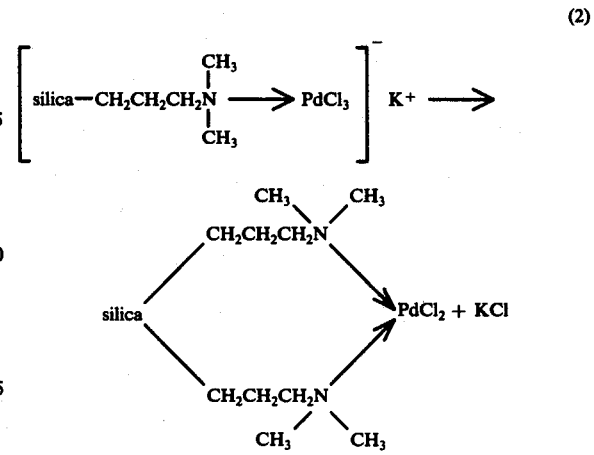

The insoluble oxide-bound metal compound complexes may be seen to comprise an insoluble functionalized oxide containing basic functional groups and chemically bonded to some of the functional groups are metal atoms, the metals having been set forth hereinabove. The bonding occurs as a result of coordination of the functional group of the oxide to the metal. The metal atoms preferably have chemically bonded thereto at least one ligand, the ligands also having been set forth hereinabove. For example, the insoluble metal compound complex set forth in equation (2) has two Cl ligands connected to the Pd atom and also two functional groups. Further, it could have one Cl ligand and three functional groups, or, as in the complex of equation (1); three Cl ligands and one functional group. On the other hand, the insoluble metal compound complexes may have a total of three, five, six, seven, or eight ligands and functional groups. At least one functional group must be present.

The insoluble oxide-bound metal compound complex is further characterized by its quantitive composition as set forth above.

The insoluble oxide-bound metal compound complexes are used herein as catalysts in carrying out the present organic compound conversion reactions. Said reactions are those which are catalyzed by soluble compounds of the metals set forth hereinbefore in homogeneous catalysis. For example, one such conversion reaction is hydrogenation, involving compounds having carbon-to-carbon unsaturation, as in the conversion of acetylenes, olefins, and diolefins, using complexes containing compounds of platinum, palladium, ruthenium and/or rhodium. For carrying out catalytic reactions generally, complexes containing as the central metal atom any of the metal described in the preceding paragraphs are of use.

Other catalytic reactions of the present invention include carbon monoxide-insertion reactions, double bond isomerizations, vinyl ester interchange reactions, and olefin (e.g. ethylene) oxidation reactions. Further examples of reactions of the present invention include olefin hydroformylation, comprising the reaction of an olefin with carbon monoxide and hydrogen in the presence of complexes containing nickel, cobalt, or rhodium carbonyl moieties; olefin dimerization and polymerization in the presence of nickel or rhodium chloride-containing complexes; olefin hydrocarboxylation, hydroesterification, and hydrocyanation in the presence of complexes containing a metal carbonyl moeity, or metal hydrocarbonyl moiety, or metal phosphine-substituted carbonyl moiety; conversion of CO and $H_2$, or alcohol and CO and $H_2$, to mixtures of hydrocarbons and/or alcohols; hydroquinone synthesis from acetylenes, carbon monoxide, and water; or the cyclooligomerization of acetylene to benzene and the like; the cyclooligomerization of butadiene to cyclooctadiene; or the carbonylation of acetylenes and olefins to acids. Also, acetylenes may be hydrated over ruthenium chloride-containing complexes. It will be apparent that many of these reactions involve the conversion of unsaturated compounds, particularly of unsaturated hydrocarbons like olefins and acetylenes. Referring again to ethylene oxidation, this reaction may be run in several ways; thus, ethylene may be oxidized in aqueous solution to produce acetaldehyde, or it may be oxidized in methanol solution to give vinyl methyl ether, or in acetic acid solution to produce vinyl acetate.

In view of the fact that the complex catalyst for use herein may contain some functional groups, i.e., basic groups, as well as metal compound groups, it follows that the complex may be a dual functional catalyst containing two types of sites, basic sites and metal compound sites. Functionalized zeolites can contain acidic sites in addition to the metal compound sites. it is thus useful to catalyze polystep catalytic organic reactions at low temperature and in the liquid phase. In such a reaction, one type of catalytic site catalyzes a reaction step different from that catalyzed by another type of site. The different types of sites are separated by distances of the order of molecular dimensions.

In some reactions, both liquid and gaseous reactants take part and are suitably catalyzed by the complexes. In all reactions, ease of catalyst separation by conventional operations of filtration, decantation, or centrifugation is a characteristic, whether the products and/or reactants are liquid or gaseous. The reactions may be carried out in conventional fixed bed flow reactors, or in continuously stirred flow reactors, or in batch reactors.

In general, organic compounds may be catalytically converted in the presence of the above heterogeneous catalyst materials over a wide range of catalytic conversion conditions, including a reaction temperature of from about $-80°$ C, to about $400°$ C, preferably from about $-20°$ C to about $350°$ C, a reaction pressure of from about 0.1 atmosphere to about 10,000 atmospheres, preferably from about atmospheric to about 1000 atmospheres, and a contact time between about 0.1 second and about 2 hours, preferably between about 1 second and about 1 hour.

In particular, when the conversion of organic compound (e.g. hydrocarbon compound) by the present method is hydroformylation, catalytic conversion conditions should be maintained within certain critical ranges, including a temperature of from about $25°$ C to about $300°$ C, preferably from about $75°$ C to about $200°$ C, a pressure of from about atmospheric to about 150 atmospheres, preferably from about 30 atmospheres to about 100 atmospheres, a contact time of from about 5 minutes to about 2 hours, preferably from about 12 minutes to about 1 hour. During hydroformylation in the presence of the above heterogeneous catalyst, a hydrogen/CO mole ratio should be maintained at between about 0.3 and about 3, preferably between about 1 and about 2; and a hydrogen/organic compound (e.g. hydrocarbon compound) ratio should be maintained at from about 0.5 to about 10 scf/bbl, preferably from about 1 to about 5 scf/bbl.

Further, when the conversion of organic compound (e.g. hydrocarbon compound) by the present method is olefin dimerization, catalytic conversion conditions should be maintained within certain critical ranges, including a temperature of from about $-80°$ C to about $50°$ C, preferably from about $-20°$ C to about $20°$ C, a pressure of from about 0.1 atmosphere to about 100 atmospheres, preferably from about atmospheric to about 10 atmospheres and a contact time of from about 0.1 second to about 10 seconds, preferably from about 1 second to about 5 seconds. When the conversion is Fischer-Tropsch, catalytic conversion conditions should be maintained within different ranges, including a temperature of from about $100°$ C to about $400°$ C, preferably from about $150°$ C to about $350°$ C, a pressure of from about 0.1 atmosphere to about 10,000 atmospheres, preferably from about atmospheric to about 1000 atmospheres, a contact time of from about 4 seconds to about 80 seconds, preferably from about 20 seconds to about 60 seconds and a hydrogen/CO mole ratio of from about 0.2 to about 5, preferably from about 1 to about 3.

It is noted that a particular advantage of the oxide-bound metal complexes used in the present invention is their high thermal stability which allows their use in reactions at temperature in which liquid phase is not easily obtained or at temperatures which would be high enough to degrade or collapse the pore structure of polymer-bound metal complexes. Also, an advantage of the amine functional groups, in comparison with phosphine functional groups, is the high oxidative stability of the former.

In order to more fully illustrate the present invention, the following specific examples are presented. Said examples, it will be appreciated, are not meant to be, and should not be taken as, unduly limiting in any way.

EXAMPLE 1

A 50 gram portion of small-pore silica was suspended in 250 ml. of xylene containing 10 ml. of N-(β-aminoethyl)-γ-aminopropyltrimethoxysilane. It was then heated to reflux (approx. 69° C) for 4 hours and cooled to room temperature. The solvent was decanted and the product was washed three times with 250 ml. portions of n-hexane. The product was then suspended in 125 ml. of 88% formic acid and 100 ml. of 37% formaldehyde. The resulting suspension was refluxed for 6 hours and cooled. The solvent was decanted and the product washed with water until neutral and then boiled in 300 ml. of water for 1 hour. The water was then decanted and the product washed two times with 300 ml. portions of acetone and dried in a vacuum oven at 125° C for 2 hours. Yield was 53.8 grams of substance having the structural formula:

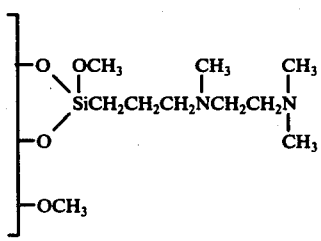

Analysis of the above product showed 0.3% N.

Five grams of the above functionalized oxide product was suspended in 150 ml. benzene through which CO had been bubbled for 15 minutes. A 0.15 gram portion of [Rh(CO)₂Cl]₂ was completely dissolved therein and the mixture was warmed to 50°-55° C for 16 hours and then cooled. The brown product was filtered out, washed and dried. Analysis of this product showed 1.86%C, 1,63%H and 0.26%Rh.

EXAMPLE 2

A 15.0 gram portion of the functionalized oxide of Example 1 was suspended in 200 ml. benzene through which CO had been bubbled for 15 minutes. A 0.83 gram portion of [Rh(CO)₂Cl]₂ was completely dissolved in this system. The resulting mixture was then heated to about 50°-55° C for 16 hours and cooled. The brown product was discernable from the clear, colorless supernatant solution and was filtered out, washed with benzene, methanol and petroleum, ether, and dried under vacuum at 120° C for ½ hour. Analysis of this product showed 1.86%C, 1.63%H and 0.81%Rh.

EXAMPLE 3

A 50 gram portion of a commercial large-pore silica was suspended in 300 ml. concentrated HCl; the mixture was heated to reflux (107° C) for 4 hours and then cooled. The silica was filtered out, washed with distilled water until the wash water was neutral, washed with acetone, and dried in a vacuum oven at 125° C for 16 hours. Yield was 47.75 grams (loss was probably mechanical). This material was then suspended in 300 ml. toluene; 27.5 grams dichlorodimethylsilane was dissolved in 100 ml. toluene and added. The mixture was then heated to reflux (104° C) for 4 hours and cooled. The mixture was reduced to a volume of 100 ml. on a rotary evaporator at about 90° C and about 20 mm. Hg pressure. A 10 gram portion of N-(β-aminoethyl)-γ-aminopropyltrimethoxy-silane was dissolved in 100 ml. toluene and added to the above mixture. All volatile liquids were then removed by distillation in a rotary evaporator. Yield was 56.4 grams. An 18.3 gram portion of this material was placed in a glass tube and heated to 150° C for 2 hours while air was drawn through the tube at about 1 liter/minute. Yield was 17.7 grams. This product was then suspended in 45 ml. of 91% formic acid and 36 ml. of 37% formaldehyde solution. The mixture was stirred and heated to reflux (89° C) for 6 hours and then cooled. The product was filtered out and washed with distilled water until the wash was neutral. It was then stirred in water at 90° C for 1 hour, filtered, washed with acetone and dried in a vacuum oven for 3 hours. Yield was 15.1 grams (most loss was probably mechanical). Analysis of this product showed 3.54% C, 1.05%H, and 0.5% N.

The initial step of refluxing in HCl was to convert some surface hydroxyl groups to surface chloride groups and thus activate the surface for condensation reactions. The condensation with dimethyldichlorosilane creates a surface on which some pairs of surface hydroxyls or chlorides are converted to surface methyls as follows:

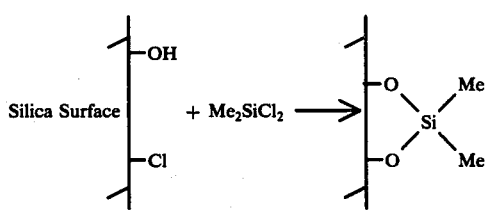

This made the surface less acidic and partially changed it from hydrophilic to hydrophobic. In addition, the following modifications resulted:

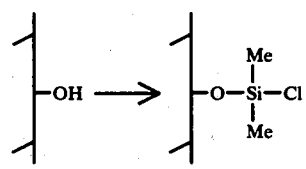

This produced a site good for further condensation since it is flexible and reduces steric requirements in the next step and also causes the final ligands to be farther away from the surface.

The procedure for putting on the amine ligand gave a product in which (1) the aminosilane was partially polymerized (at the silane end) as it was deposited, and (2) this polymer was connected to the surface through more than one of the above flexible sites (and possibly to original surface sites as well). The result was a more firmly bonded ligand because a number of siloxane bonds would have to be broken for an amine function to be removed.

For the preparation of a catalyst, 5.0 grams of the above product was suspended in 150 ml. benzene through which CO had been bubbled for 15 minutes. A 0.16 gram portion of [Rh(CO)$_2$Cl]$_2$ was completely dissolved in this system; the mixture was warmed to 50°-55° C for 6 hours and cooled. The product was brown and the supernatant solution clear and colorless. The product was filtered out, washed with benzene, methanol and petroleum ether, and dried under vacuum at 120° C for ½ hour. Yield was 4.9 grams (most loss probably mechanical). Analysis of this product showed 0.81% Rh.

EXAMPLE 4

To 50 grams of silica suspended in 250 ml. xylene was added 10.4 grams N-($\beta$-aminoethyl)-$\gamma$-aminopropyltrimethoxysilane and 0.1 gram p-toluenesulfonic acid. The mixture was stirred under reflux for 4 hours, cooled, washed with n-hexane, and dried in a vacuum oven at 120° C for 16 hours. This material was then suspended in 100 ml. 88% formic acid and 75 ml. 37% formaldehyde and stirred under reflux for 16 hours. After cooling to room temperature, 100 ml. 0.1N HCl was added and the mixture stirred for 10 minutes. The silica was filtered out, suspended in water; 1N NaOH was added until the solution was neutral; and the silica was then filtered out and washed with 1 liter of water. The silica was resuspended in 400 ml. water and the mixture was concentrated by evaporation at approximately 100° C to about half of the original volume. (This step is designed to remove any silane not covalently bonded to the silica). The silica was then filtered out and dried in a vacuum oven at 120° C overnight. The product contained 4.06% C and 1.12%N.

Carbon monoxide was bubbled through 100 ml. benzene for 15 minutes, 1.29 gram Rh$_2$(CO)$_4$Cl2 was dissolved in the benzene by warming, and 9.0 grams of the above functionalized silica was added. The mixture was stirred at 60° C for 16 hours, and the silica was filtered out, washed with benzene and dried in a vacuum oven at 130° C for 2 hours. The product contained 6.84% rhodium.

EXAMPLE 5

This catalyst was prepared as in Example 4 through the stip prior to rhodium incorporation. It was further treated as described below to convert any free surface silanol groups to trimethylsilyl groups before the rhodium was incorporated. Twenty-five grams of catalyst was suspended in 250 ml. dried xylene and 10 ml. N,O-bis (trimethylsilyl)-acetamide was added with stirring. The mixture was maintained at 100° C for 4.5 hours and then at 50–55%C for 16 hours. The silica was filtered out, washed with boiling water to remove acetamide, rinsed with acetone and dried in a vacuum oven. Rhodium was then added in the same way in Example 3. The final product contained 4.55% C, 0.87% N, and 1.96% Rh.

EXAMPLE 6

Thirty grams silica, 6.25 grams N-($\beta$aminoethyl)-$\gamma$ aminopropyltrimethoxysilane, and 120 ml. benzene were charged to a 300 ml. autoclave and heated to 300° C (approx. 900 psi) with stirring for 3 hours. After cooling, the product was washed as after the condensation step in Example 4, and the synthesis was continued as in Example 4, except that a lower loading of rhodium was added. The final product contained 4.00% C, 0.55% N, and 1.26% Rh.

EXAMPLE 7

This catalyst was prepared from a portion of an intermediate material made in the preparation of the catalyst of Example 6, so the preparation was the same up to the incorporation of the metal salt. An 8.0 gram portion of the silica that had been treated with N-($\beta$- aminoethyl)-$\gamma$ -aminopropyltriethoxysilane and then with a formic acid/formaldehyde solution followed by the usual work-up was then suspended in 100 ml. of a 1/1 (vol.-/vol.) mixture of methanol/acetone through which carbon monoxide had been bubbled for 0.25 hour. Then 0.2 gram Ru (CO)$_2$ Cl$_2$ was added and the mixture was warmed with stirring to reflux temperature (58° C.). Bubbling of CO through the system was continued, an additional 100 ml solvent was added, and reflux was continued for 16 hours. The silica was filtered out, washed thoroughly with methanol, and dried in vacuo at 125° C for 0.5 hour. The catalyst contained 4.5% carbon, 0.94% hydrogen and 0.6% nitrogen.

EXAMPLE 8

This catalyst was prepared from a portion of an intermediate material made in the synthesis of the catalyst of Example 5. A 12.0 gram portion of material was removed from the preparation of the catalyst of Example 5 just prior to the treatment with N,O-bis (trimethylsilyl)-acetamide. Instead, it was suspended in 300 ml. benzene through which carbon monoxide has been bubbling for 0.25 hour and 0.15 gram dicobaltooctacarbonyl was added. Bubbling of CO was continued and the mixture was heated to 62° C for 0.5 hour, cooled, washed thoroughly with hexane and petroleum ether and dried. The product contained 4.50% carbon, 1.23% hydrogen, 1.1% nitrogen, and 0.42% cobalt.

EXAMPLE 9 gamma-Alumina was made by heating $\alpha$-alumina for 3 hours at 900° F in air. This material was treated with N-($\beta$-aminoethyl)-$\gamma$-aminopropyl-trimethoxysilane by the procedure of Example 4 and then treated with formic acid/formaldehyde and worked up, also by the procedures of Example 4. It was then treated with N,O-bis(trimethylsilyl)-acetamide by the procedure of Example 5 and then with Rh$_2$(CO)$_4$Cl$_2$ by the procedure of Example 4. The final product contained 15.0% carbon, 2.2% hydrogen, 0.32% nitrogen and 0.33% rhodium.

EXAMPLE 10

A 10 gram sample of synthetic zeolite Y is suspended in water for 4 hours and removed by filtration but allowed to stay wet and then suspended in 4 ml N-($\beta$-aminoethyl)-$\gamma$-aminopropyltrimethoxysilane, 0.03 grams p-toluenesulfonic acid, and 60 ml xylene. The mixture is stirred under reflux for 16 hours. The sample is filtered out, washed with n-hexane, and dried in a vacuum oven. It is then suspended in 200 ml. benzene through which CO has been bubbled for 15 minutes. A 0.8 gram portion of [RH(CO)₂Cl]₂ is added to the suspension. The resulting system is heated to 50°–55° C for 16 hours with continuing CO flow. The product is filtered out, washed with benzene, methanol, and petroleum ether and dried under vacuum at 120° C for 4 hours.

EXAMPLE 11

To demonstrate that the amine functional member of the catalyst for use herein may be a substituted amine, e.g. a phosphinoamine, a substituted aminosilane functionalized silica was prepared as follows:

Three hundred grams of silica gel was suspended in xylene and heated to the reflux temperature. To this was added 45 grams of chloromethyl methyl silane and the mixture was stirred and heated at reflux overnight. The mixture was cooled to about 50° C; 10.0 ml of trimethylchlorosilane was added and the mixture was allowed to cool and stand overnight. The product was isolated by filtration and washed with xylene, hexane, and petroleum ether and was found by analysis to contain 2.73% Cl, 2.07%, and 0.71% H on a weight basis.

Sixty ml. (24.7 grams) of the above product was further modified by suspending it in 60 ml. of dimethylformamide and 22.5 grams of ethylamine and heating to 150° C for 10 hours. The reaction mixture was cooled and the product isolated by filtration. It was then washed sequentially with hexane, water, dilute NH₄OH, water 1% HCl, water, dilute NH₄OH, 2% NaOH, water (until neutral), methanol, and petroleum ether. Analysis of the final product showed it to contain on a weight basis 0.18% N, 1.0% C, and 0.61% H.

Ten grams of the above amine functionalized silica was further modified by suspending it in 50 ml. of chloroform containing 10 ml. of ethylamine. To this strirred mixture was slowly added 5.0 ml. of bis-isopropyl chlorophosphine. The reaction mixture was allowed to stand overnight, the product was isolated by filtration, and washed sequentially with chloroform and petroleum ether, and dried under N₂. The final product was analyzed and found to contain on a weight basis 5.1% C, 1.5% H, 0.6% Cl, 0.13% N, and 1.1% P. This product contained amine functional members which may be referred to as aminophosphine functional members wherein attached to many nitrogen atoms which previously had hydrogen atoms associated therwith were phosphine members as substitutions for the hydrogen atoms.

EXAMPLE 12

The functionalized silica of Example 11 was used to make a catalyst for the dimerization of propylene. Fourteen ml. (5.4 grams) of the functionalized silica was suspended in 100 ml. of chlorobenzene and 100 ml. of a 0.0026 M solution of Ni(acac)₂ in chlorobenzene was added. The solution was refluxed with gentle stirring for 2 hours and cooled. The supernatent liquid was decanted in a drybox and the solid, after washing with 100 ml. chlorobenzene, was vacuum dried. Analysis on a weight basis was 0.84% P, and 0.24% Ni.

The catalysts for use herein are useful in organic compound conversion, such as, for example, hydroformylation, oxidation, oligomerization, dimerization, hydrogenation, Fischer-Tropsch hydrocarbon synthesis and others. They exhibit excellent thermal stability up to a temperature of about 400° C, while the heterogeneous resin catalysts are stable only up to about 200° C.

For the purpose of illustrating the organic compound conversion of the present invention, the following test procedure was adapted:

Each test was conducted in a stirred 300 ml. autoclave whereby liquids and gases could be added and removed while the autoclave reaction system was under pressure. In each test, 1 to 2 grams of catalyst and 90 ml. solvent, e.g., benzene or 1:8 (volume/volume) methanol:benzene, were charged to the reactor, which was then pressure-tested with CO and vented. The system was heated to reaction temperature and then pressurized with 1:1 hydrogen:carbon monoxide. Then 20 ml. 1:1 1-hexane:n-octanal was added and the reaction started. Pressure was controlled at 1000 psi, or gas was added periodically so that the pressure fluctuated between about 900 and 1000 psi. Samples were withdrawn and the total product analyzed as by gas chromatography on a Carbowax 1000 column, and C₆ hydrocarbons on a TCP column. Liquid samples were analyzed for Rh and N. Used catalysts were analyzed for Rh, C and N.

Since the formation of aldehydes and alcohols from olefins can be shown to conform to the following scheme, the absolute values of all the rate constants of the reactions were determined.

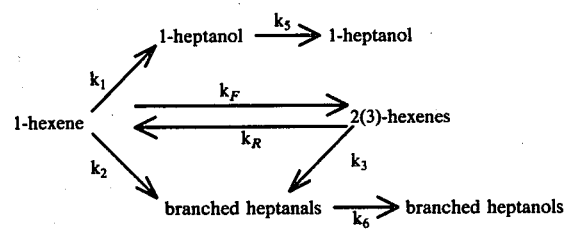

The n-octanol was included in the reaction mixtures for ease of kinetic evaluation of the catalysts.

Assuming that aldehyde diacetals were in rapid equilibrium with the corresponding aldehydes, the hydrogenation rate was measured by the disappearance of the total thereof. $S_L = (100\ k_1/k_1 + k_2)$ was a measure of the linearity of the hydroformylation products from 1-olefin. $S_I = (100\ k_F/k_1 + k_2 + k_F)$ was a comparison of the rates of isomerization and hydroformylation of 1-olefins. These two functions are important because in most applications normal aldehydes are preferred. $S_{AC}$ was defined as the percent diacetal in the linear product at the specified time. $S_{AL}$ was defined as the ratio of the rate of "steady-state" alcohol formation to the rate of "steady-state" total olefin conversion. The specific rate constants $k_1$ and $k_2$, corrected for Rh loading, reaction volume, etc., gave a measure of the relative activities of the catalysts tested.

Results of the organic compound conversion test hereinabove defined on the catalyst samples prepared by examples herein are tabulated in Table I. For comparison, an amine functionalized polymer

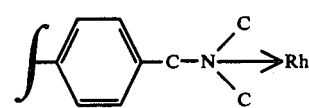

was used as a catalyst as well. The table clearly shows somewhat lower activity for the polymer catalyst and its lack of activity for the formation of acetate.

TABLE I

Organic Compound Conversion Test[1] of Catalyst Species

| Catalyst of Example | $S_L$ | $S_I$ | $S_{AC}$[4] | $S_{AL} \times 10^3$ | $(k_1 + k_2) \times 10^3$ | Time[5] | Conversion[6] |
|---|---|---|---|---|---|---|---|
| 3 | 75.6 | 55.8 | 1 | 0 | 357 | 2.5 | 99 |
| 3[2] | 71.8 | 60.8 | 2.7 | 0 | 530 | 4.3 | 100 |
| 4 | 79.6 | 60.7 | 19 | 1.3 | 136 | 7.4 | 100 |
| 4[3] | 71.5 | 82.8 | — | 2.8 | 52 | 21 | 98 |
| 5 | 71.2 | 63.5 | 31 | approx. 1 | 910 | 2.5 | 99 |
| 6 | 74.8 | 46.8 | 0.2 | 9.4 | 396 | 2.0 | 99 |
| (Polymer) | 74 | 67 | 0 | 0 | 154 | 6.0 | 84 |

[1]Hydroformylation of 1-hexene at 100° C, 1000 psi and with methanol/benzene solvent.
[2]Catalyst from above run re-used after cleaning by 1 hour reflux in MeOH/benzene
[3]Hydroformylation of 1-hexene at 100° C, 1000 psi and with benzene solvent.
[4]At time indicated.
[5]Time of run in hours
[6]Total olefin conversion.

EXAMPLE 13

Propylene was dimerized in a vertical downflow reactor over 2 cc of the catalyst of Example 12 diluted with 2 cc of 50/80 mesh Vycor chips. The catalyst was first pretreated with a solution of 0.2 M (diethylamino) di-isopropyl phosphine at 0° C. A 58% propylene/42% propane mixture was fed at a rate of 50 ml/minute over the catalyst together with a solution of 0.052 M aluminum sesquichloride in chlorobenzene at a rate of 7.3 ml/hour. This corresponds to 3 WHSV based on total catalyst and 1250 WHSV based on nickel. The conversion remained essentially constant at about 50% for 6.5 hours and the selectivity of dimethyl butenes varied between 23 and 70%. Typical product compositions were 88% dimers, 8% trimers, and 4% higher oligomers.

To further illustrate an organic compound conversion process utilizing the catalyst of the present invention, a Fischer-Tropsch reaction system was employed with catalysis therein by the catalyst hereof. Reaction conditions and results thereof are listed in Table II. Under these temperature conditions, a polymer bound metal complex would not be usuable because of the thermal instabiity of the polymer.

TABLE II

| Catalyst of Example | Reactants | Pressure, psig. H$_2$ | Pressure, psig. CO | Temperature, °C | Time[1] | Yield[2] |
|---|---|---|---|---|---|---|
| 7 | 1-butanol[3] | 500 | 500 | 300 | 12.5 | 6.8 |
| 7 | n-propanol | 500 | 500 | 300 | 96 | approx. 6 |
| 7 | 1-hexene/ n-propanol | 500 | 500 | 300 | 96 | approx. 5[4] |
| 8 | 1-octanol/ 1-hexene[5] | 500 | 500 | 300 | 26 | approx. 5[6] |

[1]Reaction time in hours.
[2]Percent yield of products having a higher boiling point than the reactants (not including hydroformylation products).
[3]Benzene solvent.
[4]Hydroformylation products also noted.
[5]Methanol and 1,2,4-trimethylbenzene solvents.
[6]Hydroformylation and olefin isomerization products also noted.

What is claimed is:

1. A method for olefin dimerization which comprises contacting said olefin under conditions effective for dimerization with a catalyst comprised of a substrate or a porous refractory oxide, said substrate having surface hydroxyl groups, a minimum surface area of about 10 m$^2$/g and pores with a minimum pore diameter of about 5 Angstrom Units, said substrate being modified by at least one amine functional member, containing the element silicon, coordinated to a metal function of a transition metal selected from the group consisting of Group VIII metals of the Periodic Table of Elements, said amine functional member acting as a bridging member between said substrate and said metal function, as a ligand covalently bonded to said substrate.

2. The method of claim 1 wherein the substrate of said catalyst has a minimum surface area of about 200 m$^2$/g and has a minimum pore diameter of 100 Angstrom Units.

3. The method of claim 1 wherein the substrate of said catalyst has a major component of silica or alumina.

4. The method of claim 1 wherein the substrate of said catalyst is selected from the group consisting of alumina, silica, silica combined with an oxide of a metal of Groups IIA, IIIA, IVA, IIIB, IVB, or VB of the Periodic Table of Elements, open lattice clays and crystalline aluminosilicates.

5. The method of claim 4 wherein the substrate of said catalyst is silica or silica combined with an oxide of a metal of Groups IIA, IIIA, IVA, IIB, IVB, or VB or the Periodic Table of Elements.

6. The method of claim 4 wherein the substrate of said catalyst is a crystalline aluminosilicate.

7. The method of claim 6 wherein said crystalline alminosilicate is a synthetic zeolite.

8. The method of claim 6 wherein said crystalline aluminosilicate is a natural zeolite.

9. The method of claim 4 wherein the substrate of said catalyst is alumina.

10. The method of claim 4 wherein the substrate of said catalyst is silica and the metal function of said catalyst is rhodium or ruthenium.

11. The method of claim 1 wherein the amine functional member of said catalyst is made from a compound selected from the group consisting of N-(β-aminoethyl)-γ-aminopropyltrimethoxysilane and N-(β-aminoethyl) -γ-aminopropyltriethoxysilane.

12. The method of claim 1 wherein said amine functional member is a phosphinoamine.

13. The method of claim 2 wherein said amine functional member is a phosphinoamine.

14. The method of claim 3 wherein said amine functional member is a phosphionamine.

15. The method of claim 4 wherein said amine functional member is a phosphinoamine.

16. The method of claim 1 wherein the conditions effective for said dimerization include a temperature of from about -80° C to about 50° C, a pressure of from about 0.1 atmosphere to about 100 atmospheres and a contact time of from about 0.1 second to about 10 seconds.

17. The method of claim 2 wherein the conditions effective for said dimerization include a temperature of from about -80° C to about 50° C, a pressure of from about 0.1 atmosphere to about 100 atmospheres and a contact time of from about 0.1 second to about 10 seconds.

18. The method of claim 3 wherein the conditions effective for said dimerization include a temperature of from about -80° C to about 50° C, a pressure of from about 0.1 atmosphere to about 100 atmospheres and a contact time of from about 0.1 second to about 10 seconds.

19. The method of claim 4 wherein the conditions effective for said dimerization include a temperature of from about -80° C to about 50° C, a pressure of from about 0.1 atmosphere to about 100 atmospheres and a contact time of from about 0.1 second to about 10 seconds.

20. The method of claim 16 wherein said olefin is propylene.

21. The method of claim 17 wherein said olefin is propylene.

22. The method of claim 18 wherein said olefin is propylene.

23. The method of claim 19 wherein said olefin is propylene.

24. The method of claim 12 wherein the conditions effective for said dimerization include a temperature of from about −80° C to about 50° C, a pressure of from about 0.1 atmosphere to about 100 atmospheres and a contact time of from about 0.1 second to about 10 seconds and said olefin is propylene.

25. The method of claim 13 wherein the conditions effective for said dimerization include a temperaure of from about -80° C to about 50° C, a pressure of from about 0.1 atmosphere to about 100 atmospheres and a contact time of from about 0.1 second to about 10 seconds and said olefin is propylene.

26. The method of claim 14 wherein the conditions effective for said dimerization include a temperature of from about -80° C to about 50° C, a pressure of from about 0.1 atmosphere to about 100 atmospheres and a contact time of from about 0.1 second to about 10 seconds and said olefin is propylene.

27. The method of claim 15 wherein the conditions effective for said dimerization include a temperature of from about -80° C to about 50° C, a pressure of from about 0.1 atmosphere to about 100 atmospheres and a contact time of from about 0.1 second to about 10 seconds and said olefin is propylene.

28. The method of claim 1 wherein said olefin is contacted with said catalyst in the presence of an aluminum alkyl chloride.

29. The method of claim 28 wherein said aluminum alkyl chloride is aluminum sesquichloride.

* * * * *

UNITED STATES PATENT AND TRADEMARK OFFICE
CERTIFICATE OF CORRECTION

PATENT NO. : 4,053,534  
DATED : October 11, 1977  
INVENTOR(S) : THOMAS OWEN MITCHELL and DARRELL DUAYNE WHITEHURST Page 1 of 2

It is certified that error appears in the above-identified patent and that said Letters Patent are hereby corrected as shown below:

| | |
|---|---|
| Column 7, line 50 | "moeity" should read --moiety--. |
| Column 8, line 7 | "it" should read --It--. |
| Column 9, line 57 | "1,63%H" should read --1.63%H--. |
| Column 11, line 57 | "stip" should read --step--. |
| Column 13, line 49 | "therwith" should read --therewith--. |
| Columns 15 and 16, Table I | Under "Catalyst of Example" insert --9-- between "6" and "(Polymer)". |
| | Under "$S_L$" insert --73.1-- between "74.8" and "74". |
| | Under "$S_I$" insert --56.3-- between "46.8" and "67". |
| | Under "$S_{AC}(4)$" insert --0-- between "0.2" and "0". |
| | Under "$S_{AL}$ x $10^3$" insert -- - -- between "9.4" and "0". |
| | Under "$(k_1 + k_2)$ x $10^3$" insert --1,237-- between "396" and "154". |
| | Under "Time$(5)$" insert --2.0-- between "2.0" and "6.0". |
| | Under "Conversion$(6)$" insert --99-- between "99" and "84". |

UNITED STATES PATENT AND TRADEMARK OFFICE
CERTIFICATE OF CORRECTION

PATENT NO. : 4,053,534
DATED : October 11, 1977
INVENTOR(S) : THOMAS OWEN MITCHELL and
DARRELL DUAYNE WHITEHURST It is certified that error appears in the above-identified patent and that said Letters Patent are hereby corrected as shown below:

| | | |
|---|---|---|
| Column 15, | Claim 1, line 3 | "or" should read --of--. |
| Column 16, | Claim 5, line 3 | "IIB" should read --IIIB--. |
| Column 16, | Claim 7, line 2 | "alminosilicate" should read --aluminosilicate--. |

Signed and Sealed this

Second Day of May 1978

[SEAL]

Attest:

RUTH C. MASON
Attesting Officer

LUTRELLE F. PARKER
Acting Commissioner of Patents and Trademarks